US009820702B2

(12) United States Patent
Osherov et al.

(10) Patent No.: US 9,820,702 B2
(45) Date of Patent: Nov. 21, 2017

(54) MOVABLE SHIELD FOR REDUCING RADIATION EXPOSURE OF MEDICAL PERSONNEL

(71) Applicants:Azriel Binyamin Osherov, Ganey Tikva (IL); Israel Chermoni, Haifa (IL); Normand Robert, Toronto (CA)

(72) Inventors: Azriel Binyamin Osherov, Ganey Tikva (IL); Israel Chermoni, Haifa (IL); Normand Robert, Toronto (CA)

( * ) Notice: Subject to any disclaimer, the term of this patent is extended or adjusted under 35 U.S.C. 154(b) by 194 days.

(21) Appl. No.: 14/865,569

(22) Filed: Sep. 25, 2015

(65) Prior Publication Data
US 2016/0029980 A1 Feb. 4, 2016

Related U.S. Application Data

(62) Division of application No. 13/561,427, filed on Jul. 30, 2012, now abandoned.

(51) Int. Cl.
| | |
|---|---|
| *A61B 6/10* | (2006.01) |
| *G21F 3/00* | (2006.01) |
| *A61B 6/00* | (2006.01) |
| *A61B 6/04* | (2006.01) |

(52) U.S. Cl.
CPC ............ *A61B 6/107* (2013.01); *A61B 6/0407* (2013.01); *A61B 6/10* (2013.01); *A61B 6/4441* (2013.01); *A61B 6/487* (2013.01); *A61B 6/548* (2013.01); *G21F 3/00* (2013.01)

(58) Field of Classification Search
None
See application file for complete search history.

(56) References Cited

U.S. PATENT DOCUMENTS

| 1,874,672 | A | | 8/1932 | Wappler ........................ 376/197 |
|---|---|---|---|---|
| 3,030,508 | A | * | 4/1962 | Mort et al. ................ G21F 3/00 |
| | | | | 250/515.1 |
| 3,233,248 | A | | 2/1966 | Bushnell |
| 4,062,518 | A | | 12/1977 | Stivender et al. ......... 250/519.1 |
| 4,280,056 | A | * | 7/1981 | Renshaw .................. G21F 7/02 |
| | | | | 250/515.1 |
| 4,938,233 | A | | 7/1990 | Orrison, Jr. |

(Continued)

FOREIGN PATENT DOCUMENTS

| GB | 797297 A | * | 7/1958 | ............... A61B 6/00 |
|---|---|---|---|---|
| GB | 797297 A | | 7/1958 | ............... A61B 6/00 |

OTHER PUBLICATIONS

Lange, H.W., et al., Randomized Comparison of Operator Radiation Exposure During Coronary Angiography and Intervention by Radial or Femoral Approach, Catheterization and Cardiovascular Interventions. 67:12-16 (2006).

(Continued)

*Primary Examiner* — Michael Logie
(74) *Attorney, Agent, or Firm* — William Dippert; Laurence Greenberg; Werner Stemer

(57) ABSTRACT

An extendable shield apparatus for reducing radiation exposure of medical personnel to be used especially in hospitals is provided that comprises a base capable of being connected to a patient table of an X-ray fluoroscopy bed and a pole connected substantially vertically to the base. A dispenser for X-ray opaque blanket is supported by the pole, and a self-supporting X-ray opaque blanket capable of being extended from the dispenser.

6 Claims, 10 Drawing Sheets

(56) References Cited

U.S. PATENT DOCUMENTS

| | | | |
|---|---|---|---|
| 4,965,456 A | 10/1990 | Huettenrauch et al. | 250/515.1 |
| 5,006,718 A | 4/1991 | Lenhart | 250/519.1 |
| 5,012,114 A | 4/1991 | Sisson, Jr. | |
| 5,185,778 A | 2/1993 | Magram | 378/196 |
| 5,981,964 A * | 11/1999 | McAuley | G21F 3/00 250/515.1 |
| 6,325,538 B1 | 12/2001 | Heesch | |
| 6,435,717 B1 * | 8/2002 | Kohler | A61B 6/107 378/205 |
| 7,099,427 B2 | 8/2006 | Cadwalader et al. | |
| 7,109,505 B1 | 9/2006 | Sliski et al. | |
| 7,294,845 B2 | 11/2007 | Ballsieper | |
| 7,767,990 B2 | 8/2010 | Cadwalader et al. | |
| 7,829,873 B2 | 11/2010 | Fox et al. | |
| 2003/0091150 A1 * | 5/2003 | Barber | A61B 6/107 378/189 |
| 2003/0091152 A1 * | 5/2003 | Dietz | A61B 6/107 378/197 |
| 2005/0173640 A1 * | 8/2005 | Nascetti | A61B 6/032 250/370.09 |
| 2006/0124871 A1 | 6/2006 | Ballsieper | 250/516.1 |
| 2007/0252095 A1 | 11/2007 | Magram | |
| 2008/0031422 A1 * | 2/2008 | Barkow | A61B 6/107 378/203 |
| 2008/0073593 A1 * | 3/2008 | Fox | G21F 1/125 250/503.1 |
| 2009/0045358 A1 | 2/2009 | Arterson | 250/519.1 |
| 2009/0110152 A1 * | 4/2009 | Manzke | A61B 6/4423 378/195 |
| 2009/0232282 A1 * | 9/2009 | Belson | A61B 6/107 378/203 |
| 2010/0176318 A1 | 7/2010 | Smith | |
| 2010/0199428 A1 | 8/2010 | Guguin et al. | 5/430 |
| 2011/0064188 A1 | 3/2011 | Suzuki et al. | |
| 2011/0103555 A1 * | 5/2011 | Hunt | A61B 6/107 378/203 |
| 2011/0165269 A1 | 7/2011 | Khandkar | |

OTHER PUBLICATIONS

Brueck, M., et al. A Randomized Comparison of Transradial Versus Transfemoral Approach for Coronary Angiography and Angioplasty, JACC: Cardiovascular Interventions, vol. 2, No. 11: 1047-54 (2009).

Neill J., et al. Comparison of Radiation Dose and the Effect of Operator Experience in Femoral and Radial Arterial Access for Coronary Procedures, Am. J. Cardiol. 106:936-40 (2010).

* cited by examiner

MOVABLE SHIELD FOR REDUCING RADIATION EXPOSURE OF MEDICAL PERSONNEL

CROSS-REFERENCE TO RELATED APPLICATION

This is a divisional application of U.S. patent application Ser. No. 13/561,427, filed Jul. 30, 2012, which is incorporated by reference herein in its entirety.

FIELD OF THE INVENTION

The present invention relates to reducing exposure of medical personnel to X-ray radiation scattered by the patient body during fluoroscopic procedures.

BACKGROUND OF THE INVENTION

The harmful effect of radiation was soon recognized after the discovery of X-ray by Wilhelm Roentgen in 1895 yet the carcinogenesis potential of X-rays was not discovered till the middle of the twentieth century.

Although the acute effects of radiation are not commonly a problem, the probability of occurrence of stochastic effect leading to cancer is directly related to the radiation dose.

Stochastic effect is particularly important because there is no threshold below which, the radiation induced effect will not occur. Medical personnel involved in x-ray guided interventional procedures, including invasive and interventional cardiologists, have frequent exposure through fluoroscopy and cineangiography; many of the above are long and complex procedures. Procedures done through the radial artery or femoral approach in general, might require long fluoroscopy times and therefore greater cumulative scatter radiation to the operator and staff. Even shorter procedures done by the hundreds per year will lead to significant cumulative dose of radiation exposure to the operator. While the acute radiation exposure per case is not significant enough to be a major concern, the cumulative risk associated with a lifetime of exposure could become significant. In addition to higher cancer risk, there is increase of cataract incidence compare to the general population. In addition procedures done through radial access site are known to have on average longer fluoroscopy times. Some operators will avoid using the left radial as an access site due to the fact that they are being exposed to much higher scattered radiation compare to right radial or femoral access site procedures. It is well accepted that radial procedures are safer compare to femoral ones in regard to bleeding complication, mobility of the patients after the procedure and even lower mortality. As a consequence, avoiding using left radial due to fear of radiation exposure might prevent many patients from having radial procedures and will put them at risk for higher morbidity and mortality.

Medical personnel usually wear protective aprons, thyroid lead collar, and leaded glasses. Other radiation shields are used for protection and are deployed between the radiation source or the patient and the personnel in the catheterization laboratory.

Despite all protection measures, the operators are exposed especially to scattered radiation coming from the patient. Some operators will be exposed to radiation level higher than permitted per year (50 mSv).

U.S. Publ. Patent Application No. 20110165269: "Radiation Protection System", to Khandkar; Ashok C., discloses a shield for radiation attenuation. The shield includes a carrier suitable for topical application on human tissue, such as skin. The carrier includes an active ingredient that is homogenously dispersed throughout the carrier.

U.S. Publ. Patent Application No. 20100176318: "Shape retentive flexible radiation absorber", to Smith Peter C., discloses a composite radiation absorber made up of a rubber or rubber like matrix material filled containing a radiation absorptive element, or a plurality of radiation absorptive elements, combined with deformable and shape retentive member or members that once deformed into a desired shape will essentially retain that shape for the composite in use.

U.S. Pat. No. 7,829,873: "Lower shield for radiation protection system" to Fox, et al. discloses a radiation protection shield for protecting medical personnel from radiation being applied to a patient positioned on a table. The shield includes a frame and a primary screen including a radiation-resistant material connected to said frame.

U.S. Pat. No. 7,767,990: "Radiation attenuation system for lateral imaging", to Cadwalader, et al., discloses a radiation attenuation system for attenuating radiation during lateral radiographic imaging of an object is provided. The system includes a radiation attenuating barrier that is substantially conformable to the object and configured to at least partially cover the object.

U.S. Pat. No. 7,294,845 "Radiation protection arrangement comprising a separable cover", to Ballsieper, discloses a radiation protection arrangement for screening radiation emitted from a radiation source, especially an x-ray source. Said arrangement is provided with a screening element consisting of, or comprising, a radiation protection material, and a cover, which fully surrounds the screening element. Said cover can be pulled over the screening element and completely separated from the same. As the cover can be changed, the radiation protection arrangement can be kept clean and sterile in a simple manner.

U.S. Pat. No. 7,109,505: "Shaped biocompatible radiation shield and method for making same", to Sliski, et al., discloses a radiation applicator system is structured to be mounted to a radiation source for providing a predefined dose of radiation for treating a localized area or volume, such as the tissue surrounding the site of an excised tumor.

U.S. Pat. No. 7,099,427: "Radiation attenuation system", to Cadwalader, et al., discloses a radiation attenuation system for use with Computed Tomography procedures is disclosed. The system includes a shield made of a radiation attenuation material and may be useful in blocking or attenuating radiation, and assisting in the protection of at least one of a patient and a medical personnel present during the Computed Tomography procedure.

U.S. Pat. No. 5,012,114: "Radiation shield", to Sisson, Jr., discloses a radiation shield comprises a wrappable sheet of radiation-shielding material such as lead-filled plastic sheet faced on one side with a vinyl facing sheet and on the other side with a sheet of heat-resistant material.

U.S. Pat. No. 4,938,233: "Radiation shield", to Orrison, Jr., discloses a flexible shield for covering an article and attenuating the flux of electromagnetic radiation relative to the article includes a polymetric matrix charged with an attenuating filler. The shield has a transmission attenuation factor of at least 50% of a primary 100 kVp x-ray beam, a durometer of less than about 100 Shore "00" and a coefficient of sliding friction relative to the article of at least 0.15.

U.S. Pat. No. 3,233,248: "Radiation protective apron", to Bushnell, discloses a radiation controlling shield garments.

REFERENCES

Underwood E A. Wilhelm Conrad Röntgen (1845-1923) and the Early Development of Radiology. Proc R Soc Med. 1945; 38:697-706.

Kolodny A. Tissue Changes after Experimental Deep Roentgen Irradiation. Am J Pathol. 1925; 1:285-294.

Limacher M C, Douglas P S, Germano G, Laskey W K, Lindsay B D, McKetty M H, Moore M E, Park J K, Prigent F M, Walsh M N. ACC expert consensus document. Radiation safety in the practice of cardiology. American College of Cardiology. J Am Coll Cardiol. 1998; 31:892-913. Review.

Hirshfeld J W Jr, Balter S, Brinker J A, Kern M J, Klein L W, Lindsay B D, Tommaso C L, Tracy C M, Wagner L K, Creager M A, Elnicki M, Hirshfeld J W Jr, Lorell B H, Rodgers G P, Tracy C M, Weitz H H; ACCF/AHA/HRS/SCAI clinical competence statement on physician knowledge to optimize patient safety and image quality in fluoroscopically guided invasive cardiovascular procedures. A report of the American College of Cardiology Foundation/American Heart Association/American College of Physicians Task Force on Clinical Competence and Training. American College of Cardiology Foundation; American Heart Association; American College of Physicians. J Am Coll Cardiol. 2004; 44:2259-82.

Vano E, Kleiman N J, Duran A, Rehani M M, Echeverri D, Cabrera M. Radiation cataract risk in interventional cardiology personnel. Radiat Res. 2010; 174:490-5.

Mann J T 3rd, Cubeddu G, Arrowood M. J Invasive Cardiol. Operator Radiation Exposure in PTCA: Comparison of Radial and Femoral Approaches. J Invasive Cardiol. 1996; 8 Suppl D:22D-25D.

Lange H W, von Boetticher H. Randomized comparison of operator radiation exposure during coronary angiography and intervention by radial or femoral approach. Catheter Cardiovasc Interv. 2006; 67:12-16.

Brueck M, Bandorski D, Kramer W, Wieczorek M, Höltgen R, Tillmanns H. A randomized comparison of transradial versus transfemoral approach for coronary angiography and angioplasty. JACC Cardiovasc Interv. 2009; 2:1047-54.

Neill J, Douglas H, Richardson G, Chew E W, Walsh S, Hanratty C, Herity N. Comparison of radiation dose and the effect of operator experience in femoral and radial arterial access for coronary procedures. Am J Cardiol. 2010; 106:936-40.

Mercuri M, Mehta S, Xie C, Valettas N, Velianou J L, Natarajan M K. Radial artery access as a predictor of increased radiation exposure during a diagnostic cardiac catheterization procedure. JACC Cardiovasc Interv. 2011; 4:347-52.

Politi L, Biondi-Zoccai G, Nocetti L, Costi T, Monopoli D, Rossi R, Sgura F, Modena M G, Sangiorgi. Reduction of scatter radiation during transradial percutaneous coronary angiography: A randomized trial using a lead-freeradiation shield. Catheter Cardiovasc Interv. 2012; 79:97-102.

Venneri L, Rossi F, Botto N, Andreassi M G, Salcone N, Emad A, Lazzeri M, Gori C, Vano E, Picano E. Cancer risk from professional exposure in staff working in cardiac catheterization laboratory: insights from the National Research Council's Biological Effects of Ionizing Radiation VII Report. Am Heart J. 2009; 157:118-24

Roguin A, Goldstein J, Bar O. Brain malignancies and ionising radiation: more cases reported. EuroIntervention. 2012; 8:169-70.

Azriel B. Osherov Peter Seidelin, Rafael Wolff Graham Wright Bradley H. Strauss Normand Robert. A Novel Technique to Reduce the Operator's Exposure to Scattered Radiation in Transradial Coronary Procedures. Submitted for publication EuroIntervention January 2012, presented at the EuroPCR conference Paris 15-18 May 2012.

Lange H W, von Boetticher H. Reduction of operator radiation dose by a pelvic lead shield during cardiac catheterization by radial access: comparison with femoral access. JACC Cardiovasc Interv. 2012; 5:445-9.

SUMMARY OF THE INVENTION

The current invention discloses a movable device that holds a radiation protection drape for reducing exposure and protecting medical personnel from hazardous X-ray radiation scattered by the patient during fluoroscopy. The device enables positioning an X-ray opaque drape such that it covers the patient in an anatomically and procedurally compatible ways that reduces significantly the scattered radiation towards the operators. The device is capable of repositioning the X-ray opaque drape according to the C-arm movement to prevent interfering with the X-ray beam and the fluoroscopy image. The device is simple to use, reusable, and intent for the invasive, diagnostic and interventional procedure done in the catheterization laboratory.

It is an aspect of the current invention to provide a movable X-ray shield apparatus for reducing exposure of medical personnel to scattered X-ray, comprising: a rail, capable of being connected to a patient table of an X-ray fluoroscopy bed; a carriage 112, capable of sliding along said rail; at least one pole, connected substantially vertically to said carriage; a bridge, capable of sliding along said at least one pole; and an X-ray opaque shield, supported by said bridge, and capable of blocking scattered X-ray radiation.

In some embodiments the opaque shield is rigid.

In some embodiments the rigid opaque shield is connected to said bridge with at least one pivot, and capable of being positioned in at least two angular positions with respect to said patient table.

In some embodiments the rigid opaque shield is optically transparent.

In some embodiments the opaque shield comprises an X-ray opaque blanket; and said X-ray opaque blanket is supported by at least one arm connected to said bridge.

In some embodiments the movable shield apparatus further comprises at least one X-ray shielding blanket or strip, capable of blocking scattered X-ray radiation from escaping the gap between said X-ray shield and said rail.

In some embodiments the movable shield apparatus further comprises a motorized actuator, capable of moving said carriage along said rail.

In some embodiments the movable shield apparatus of further comprises a motorized actuator, capable of moving said bridge along said at least one pole.

In some embodiments the movable shield apparatus further comprises a handle for moving the movable shield apparatus along said rail.

It is another aspect of the current invention to provide an extendable shield apparatus for reducing radiation exposure of medical personnel comprising: a base, capable of being connected to a patient table of an X-ray fluoroscopy bed; a pole, connected substantially vertically to said base; a dispenser for X-ray opaque blanket, supported by said pole; and a self-supporting X-ray opaque blanket, capable of being extended from said dispenser.

In some embodiments the pole is capable of moving vertically in respect to said base.

In some embodiments the pole is capable of rotating in respect to said base.

In some embodiments the extendable shield apparatus further comprises a swivel joint that allows rotating the dispenser in respect to said pole.

In some embodiments the extendable shield apparatus further comprises: a retracting motor, capable of retracting said self-supporting X-ray opaque blanket into said dispenser; and an extending motor, capable of extending said self-supporting X-ray opaque blanket out of said dispenser.

In some embodiments the self-supporting opaque blanket comprises a plurality of reed springs, capable of keeping said self-supporting opaque blanket in substantially horizontal position when extended, yet allow said blanket to bend as it is retracted into said dispenser.

In some embodiments the plurality of reed springs are the type used in retractable measuring tapes.

It is yet another aspect of the current invention to provide a fluoroscopy system comprising: a C-arm unit comprising: an X-ray tube, capable of producing X-ray beam; an X-ray imager, capable of detecting said X-ray beam; and at least one light source capable of producing at least one light beam, wherein said least one light beam is situated to mark the edge of said X-ray beam; a patient bed comprising a patient table; and an X-ray shield apparatus comprising an X-ray opaque shield for reducing radiation exposure of medical personnel.

In some embodiments the at least one light source is attached to said X-ray tube.

In some embodiments the at least one light source is attached to said X-ray imager.

In some embodiments the X-ray shield apparatus is further comprising: a light sensor, capable of sensing said at least one light beam; and at least one motorized actuator, capable of adjusting the position of said X-ray opaque shield in response to signals from said light sensor such that said X-ray opaque shield would not block said X-ray beam.

In some embodiments the X-ray shield apparatus is further comprising: an X-ray sensor, capable of sensing said X-ray beam; and at least one motorized actuator, capable of adjusting the position of said X-ray opaque shield in response to signals from said X-ray sensor such that said X-ray opaque shield would not substantially block said X-ray beam.

In some embodiments the X-ray shield apparatus is further comprising: a rail, capable of being connected to a patient table of an X-ray fluoroscopy bed; a carriage, capable of sliding along said rail; at least one pole, connected substantially vertically to said carriage; a bridge, capable of sliding along said at least one pole; and an X-ray opaque shield, supported by said bridge, and capable of blocking scattered X-ray radiation.

In some embodiments the X-ray shield apparatus is further comprising: a base, capable of being connected to a patient table of an X-ray fluoroscopy bed; a pole, connected substantially vertically to said base; a dispenser for X-ray opaque blanket, supported by said pole; and a self-supporting X-ray opaque blanket, capable of being extended from said dispenser.

In a procedure done through the Radial or femoral artery approach, there is a large portion of the patient body (this includes the lower extremities, pelvis, abdomen, chest) that is a source of scatter radiation to the operator. This portion of the patient's body may be covered with an X-ray opaque material such as lead. The X-ray opaque material may have a rectangular shape, but shapes such as square, trapezoid, hexagon, pentagon, parallelogram, oval may be used and it may have rounded corners or not. A non-disposable radiation protection drape was shown to minimize significantly the radiation scattered from a patient towards an operator and other personnel in the catheterization laboratory. It was shown that a stationary rectangular X-ray opaque material does not give the maximally scattered radiation protection for procedures done in cranial or Antero-posterior views. To overcome this limitation a device according to embodiments of the current invention holds a lead drape and enables motion of said drape in accordance to the movement of the C-arm, in a way that it will not block the radiation field yet will give the maximum scattered radiation protection. For example, in caudal views, the device moves the radiation absorbing drape down towards the patient umbilicus and in cranial views it will move the drape to cover the patient's chest.

The device according to the invention holds the radiation protection lead drapes, reduces the problem of scattered radiation from the patient by providing an efficient barrier between the source of scattered radiation and the personnel in the room. The radiation protection device reduces the radiation for radial artery approach, a femoral artery approach, both simultaneously, or for any other access site for example brachial artery, femoral, subclavian, inominate, axillary and jugular veins. Yet not limited to the above access sites.

A possible advantage of the device according to the current invention is the option to switch from one approach (e.g., radial access) another approach (e.g., femoral access), while continuing to have a significant radiation protection at all times. Its is a common opinion that in procedures done through the left radial access, the operator is exposed to significant more scattered radiation compare to right radial or femoral access, due to a closer proximity to the patient. An additional possible benefit of using the lead drape protection system in the invention is that by significantly lowering the scattered radiation to the operator in Left radial procedures it may encourage using said procedures on more patients. This may lower the patient's morbidity and mortality rates.

In most patients having coronary bypass surgery, the left internal mammary artery is used as a bypass graft. As a consequence these patients usually are having the catheterization or interventional procedure done through a femoral access site. A possible benefit of the invention is a shift towards more left radial procedures, which makes cannulation of the left radial artery more attractive, which might lead to less morbidity and mortality in patients after bypass surgery when the LIMA artery was used as a graft.

In the catheterization laboratory, the images are often acquired with the X-ray source at various positions and angles. In caudal views the source of radiation points the beam from underneath the patient, below the upper part of the patient, towards an X-ray imaging detector (an image intensifier) located above the patient, above the lower part of the patient. The most common X-ray imaging detector technologies also called X-ray imager technologies are the X-ray image intensifiers and the X-ray flat panel detector.

The x-ray imaging detector and the radiation source are connected and move together as a "C-arm" as known in the art. In cranial view, the radiation source is located underneath the table and the X-ray imager is located over the upper part of the patient. Due to the geometry/direction of the radiation beam, there is more scattered radiation towards the operator while using cranial views fluoroscopy. The movable device and radiation protection drapes disclose herein may significantly reduce the radiation scatter towards the operator in all views. If an operator uses mainly cranial acquired images and fluoroscopy during a procedure, the inventive device may move the lead drape up to cover area above the umbilicus in a way that it will not obstruct the image view and will enable better radiation protection.

The inventive device may be moved manually by the operator or be moved using motorized actuators such as electrical or hydraulic systems.

As mentioned for caudal views, a preferred placement for the drape may be from the umbilicus of the patient and down such it is not seen in the x-ray image. In cranial views, the drape may be shifted from the umbilicus toward the thorax yielding increased radiation protection. The placement of the device is not limited to the above and can be used to cover any part of the patient from head to toes in any fluoroscopic view. This can be done manually—the operator may pull the lead drape up. The amount of movement needed may be determined by using a beam of light (or a plurality of such beams) situated at the edge of the X-ray beam. The light beam(s) may be produced by a lit source(s) positioned on the X-ray source and/or the X-ray detector housing and marking the border of the X-ray beam. In order to avoid obscuring the X-ray image, the drape should not cross the light beam(s).

Another less preferable option is to use fluoroscopy for drape placement. The same positioning process: pulling the lead up and down along the longitudinal axis of the patient may be done automatically. A sensor for light (visible or Infra-Red light) may be used for detecting the position of the X-ray beam position and for moving the X-ray protection device using electrical or hydraulic system depending on the position in space of the detector. In that way the drape will not obstruct the fluoroscopic in any specific view.

Operating the device to pull the drape up and down (automatically—according to the light beam or user's commands) may be done while the operator is in the room or it may be done be cone remotely while the operator/technician is outside the catheterization laboratory sterile environment.

Optionally, the device comprises a hydraulic and or electrical actuator or a plurality of actuators to enable motorized movement up or down along the longitudinal axis of the patient, and optionally in other directions such as horizontal, around the patient in a circular manner or combination of the above.

Optionally, placement of the drape may be done using a camera that detects the place where the light beam illuminating the patient. Optionally, an operator inside the room or outside the room (and preferably at a distance from the operating table), by watching the images (of the light beam on the patient) provided by the camera is able to remotely move the device to get maximum scattered radiation reduction/protection without compromising the X-ray image. This can be done without turning on the X-ray tube, thus avoiding exposing the patient to radiation.

Optionally, placement of the drape may be done using X-ray radiation sensors attached to the edge of the drape that detect the higher level of radiation that occurs if the drape is at the edge of the primary radiation beam.

Optionally, placement of the drape may be done by the detecting its presence at the edge of the X-ray image.

In an exemplary embodiment the drape is approximately 15×31 inch (40×80 cm). However, the size is not limited to this size and can range for example from 10 cm width and 30 cm length to more than 60 cm or 100 cm.

This X-ray opaque rectangle may be attached to a movable device and may be able to move along the longitudinal axis of the patient while lying on the table in the catheterization laboratory. Adjustments to the position of the lead may be done by operating the device.

The device may move on a rail located on either side of the table. Optionally, the drape is inserted into a sterile bag (for example a nylon bag or any kind of disposable sterile cover or bag). This will enable the device to be on top of the patient's sterile drape (or underneath).

Optionally, X-ray opaque materials used are made of lead of 0.25 to 0.5 mm in thickness. However thickness is not limited to these values may range from 0.01 to 10 millimeters in thickness, and more preferably 0.2-0.7 mm lead equivalent thickness, thus fulfilling the standards requirements for radiation protection for both 130 and 150 kVp of radiation, yet not limited to the above energy levels. Optionally, multiple layers of X-ray absorbent/blocking materials may be used. Optionally, the attenuating material may contain a plurality x-ray absorbing atomic elements.

In some embodiments, in order to maximize the effect of reducing the radiation two elongated overlapping drapes will cover the patient. One stationary from the umbilicus and down and the other attached to the inventive device that can move the X-ray opaque drape up along the length of the patient to cover the chest or down to the umbilicus area.

The X-ray opaque drapes may be inserted inside a sterile cover (cover may be made of Nylon, but the cover is not limited to nylon and may be made from plastic, paper, cloth or other disposable sterile materials) and can be put on the patient (underneath or on top the large sterile drape that cover the patient during the procedure).

If there is a need to use the femoral artery for access site, the lower drape may be flipped in the middle and folded in two to expose the right femoral artery. The lower drape may be made of two (or three) smaller rectangles, each in its protective cover, that are connected to each other for example by sutures, Velcro, clips, or similar constraints. This may enable flipping one rectangle on top the other frequently without damaging the attenuating layer within the drape. After insertion of the sheath to the femoral artery, if the access site is needed for temporary pacemaker insertion, intra aortic balloon pump, Swan Ganz catheter, etc., the drape may be flip back to give the maximal radiation protection. Similar steps may be performed to use the left femoral artery for access.

The device may be attached to the operating table in a movable way, to the left or right side of the table. The device may be attached permanently or temporarily or not at all. The design of the drapes preferably meets the requirements of using it in a sterile environment. While the X-ray opaque drapes are preferably reusable, the sterile nylon bags may be disposable or may be replaced between patients to keep sterility.

Preferably, X-ray opaque drape comprises at least one layer of lead having thickness of 0.25-0.5 mm lead equivalent as per regulatory requirements of the high standards for protection from radiation of energy of 130 kVp and 150 kVp. The invention is not limited to those energy levels and may include lead drapes designs to protect against higher or lower levels of radiation.

An optional sensor attached to the unit may detect a light beam coming from the radiation detector or from the X-ray imager and transmit a signal to the motors for automatically moving the shield.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

Other features which are considered as characteristic for the invention are set forth in the appended claims.

Although the invention is illustrated and described herein as embodied in a movable shield for reducing radiation exposure of medical personnel, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DETAILED DESCRIPTION OF THE INVENTION

Figure 1:
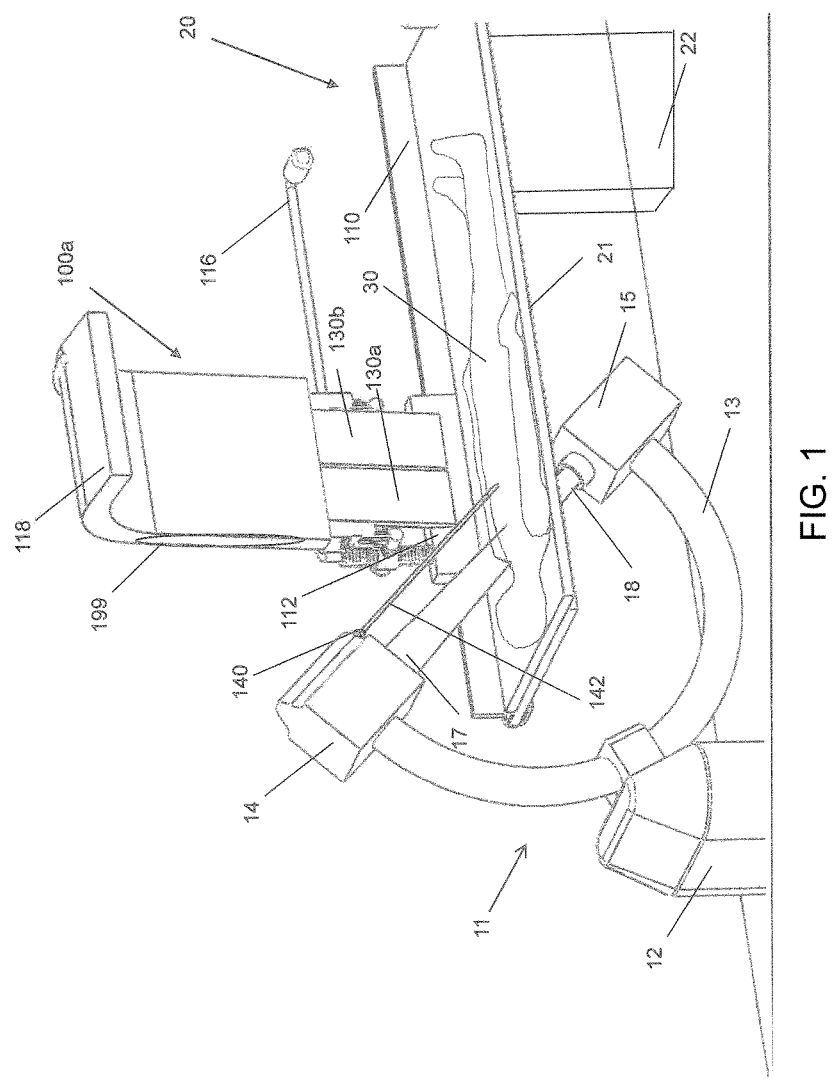
FIG. 1 schematically depicts medical system with a movable shield apparatus 100a for reducing radiation exposure of medical personnel according to an exemplary embodiment of the current invention.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The terms "comprises", "comprising", "includes", "including", and "having" together with their conjugates mean "including but not limited to".

The term "consisting of" has the same meaning as "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

In discussion of the various figures described herein below, like numbers refer to like parts. The drawings are generally not to scale. For clarity, non-essential elements were omitted from some of the drawing.

FIG. 1 schematically depicts medical system with a movable shield apparatus 100a for reducing radiation exposure of medical personnel according to an exemplary embodiment of the current invention.

System 10 is a fluoroscopy or cineangiography system as known an used for medical imaging and for performing diagnostics of interventional procedure which was improved by installing a movable shield apparatus 100a for reducing radiation exposure of medical personnel according to an exemplary embodiment of the current invention. It should be noted that movable shield apparatus 100a may be installed as upgrade to existing fluoroscopy or cineangiography system 10, or be integrated during design and manufacturing of such system.

Only the essential components of system 10 are discussed herein. System 10 comprises an X-ray C-arm unit 11 having a base 12, and a movable arc 13. Arc 13 carries X-ray tube 14 on one end and X-ray imager 15 on its other end. For drawing clarity, other parts of the X-ray imager, such as the electronics, optional cables, ECG connections, display, controls, and alkies were omitted from this and next drawings. an X-ray beam 17 is generated at the focal point within the X-ray tube 14, traverse the patient 30 and the X-ray transparent table 21 on which the patient is positioned, exits the patient as partially absorbed X-ray beam 18 and finely absorbed and detected by X-ray imager 15.

The patient 30 (not seen in some of drawings) is positioned on a movable bed 20 having a base 22 and table 21 made of X-ray transparent material. In this figure, X-ray tube 14 is seen underneath patient 30; however, rotating arc 13 may position the X-ray imager 15 above the patient.

As discussed in the background section, a substantial portion of X-ray beam 17 is scattered within the patient 30 by the tissue of the patient and scatters into random directions, thus posing health hazard to medical personnel standing near the patient.

In the exemplary embodiment depicted here, movable shield apparatus 100a comprises a rail 110 which is connected to table 21. Rail 110 runs along table 21 along its long edge. A carriage 112 is movably attached to rail. A position adjusting mechanism 114 is connected to cartridge 112 and moves along rail 110 with cartridge 114. Some additional details of position adjusting mechanism 114 are seen in the following figures.

It should be noted that optionally, movable shield apparatus 100a may be used together with other X-ray shielding devices as known in the art.

In the depicted exemplary embodiment, a rigid X-ray shield 118 is attached to the position adjusting mechanism 114. Optionally, rigid X-ray shield 118 is attached to the position adjusting mechanism 114 at pivot 120 such that rigid X-ray shield 118 may swing upwards (as seen in this figure) for easy access to the patient, as well as easy loading and discharging of patient 30. Rigid X-ray shield 118 is optionally made of optically transparent material such as lead glass or acrylic such as available for example at MarShield 4140 Morris Drive, Burlington, Ontario, Canada. Alternatively, rigid X-ray shield 118 may be made of lead or tungsten or other X-ray opaque material. It should be noted that rigid X-ray shield 118 may be made as semi rigid, or as a flexible radio-opaque blanket stretched over a rigid frame.

Optionally, shield apparatus 100a further comprises flexible or rigid X-ray shielding blanket or strips 130a and 130b are used for blocking scattered X-ray radiation from escaping the gap between rigid X-ray shield 118 and rail 110.

Optionally, cartridge 112 may be locked in position to rail 110. Optionally, cartridge 112 is fitted a quick release handle 116 to allow fast unlocking of the carriage 112 from rail 110 and moving the entire movable shield apparatus 100a along rail 110, for example such that such that rigid X-ray shield 118 is positioned over the patient's legs, and immediate medical attention may be given to patient 30 without the need to remove the patient from bed 20. Alternatively, fast access to patient 30 is possible by bringing rigid X-ray shield 118 to upward position seen in this figure, or both.

In the exemplary embodiment depicted here, movable shield apparatus 100a further comprises at least one visual indicator 140, for example, a visible laser or an LED that generates a light beam 142. Beam 142 is situated to mark the edge of X-ray beam 18 and is used by the operator to ensure that X-ray beam 18 is not obscured by rigid shield (or other shields used in this invention) without having to turn on the C-arm unit 11 and expose the patient and the medical personnel to harmful X-ray radiation.

Optionally, a light sensor 199 is used for detecting light beam 142 and indicates that shield 118 is near or within the X-ray beam 18. Alternatively, sensor 199 in an X-ray sensor, adapted to detect X-ray emitted from the X-ray source and to distinguish between such intense X-ray beam from the weaker scattered radiation. By advancing the shield and the sensor to the edge of the X-ray beam (17 and 18), adequate protection from scattered radiation and minimal interference with the X ray imaging may be achieved. Specifically, sensor 199 may be useful for automatically positioning the shield when the apparatus is motorized such as seen in FIG. 5 and FIGS. 6-9.

Figure 2:
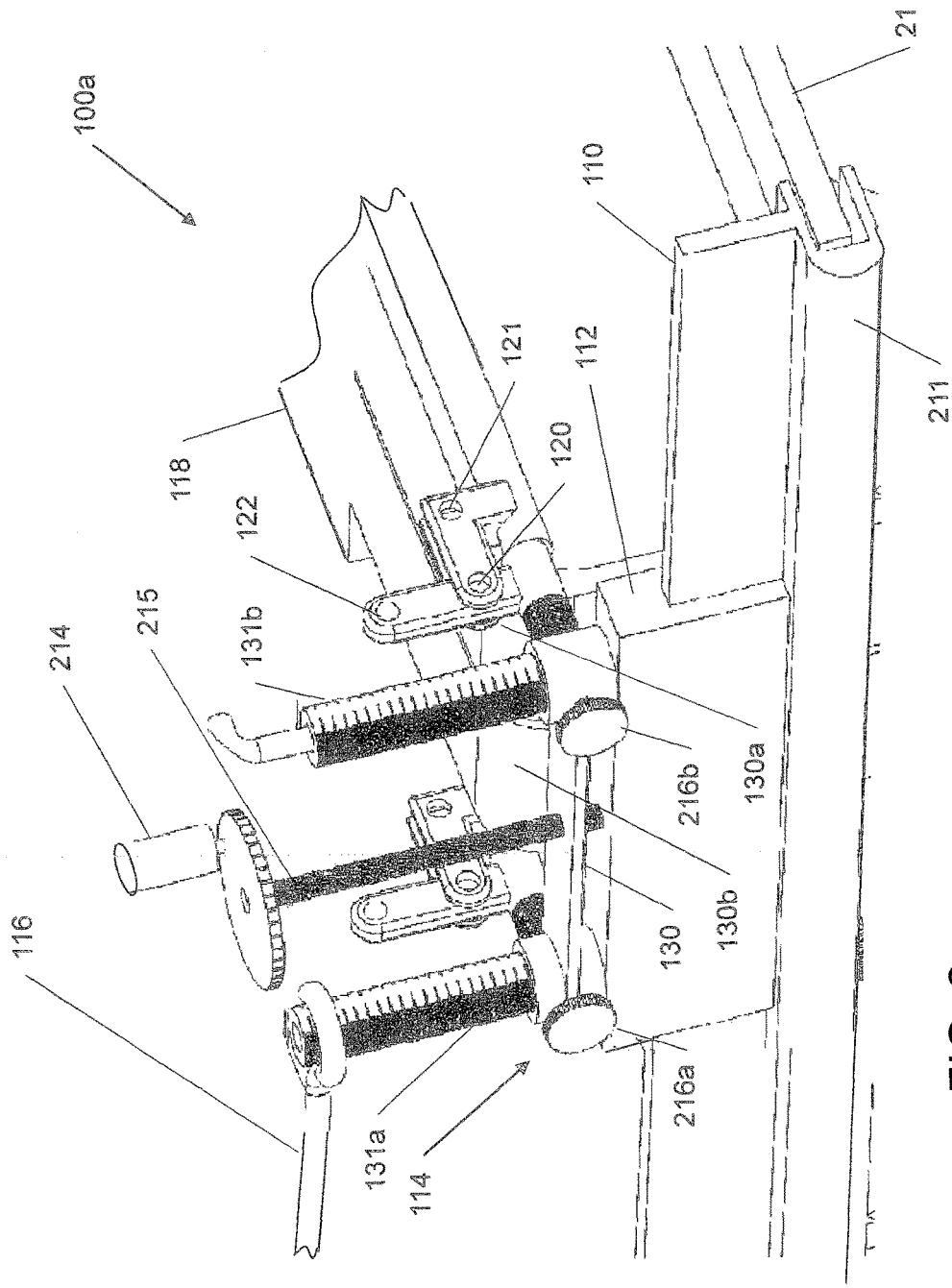
FIG. 2 schematically depicts some details of a movable shield apparatus for reducing radiation exposure of medical personnel according to an exemplary embodiment of the current invention.

FIG. 2 schematically depicts some details of a movable shield apparatus for reducing radiation exposure of medical personnel according to an exemplary embodiment of the current invention.

FIG. 2 schematically depicts the optional connector 211 that connects rail 110 to stretcher 21. Optionally, rail 110 may be connected in other ways to the stretcher or other parts of bed 20. The connection may optionally use fasteners to secure the rail to the bed. Optionally the rail may be removed for cleaning or when not needed. Alternatively, rail 110 may be permanently connected to the bed.

The height of rigid X-ray shield 118 is optionally adjusted by raising or lowering bridge 130 which slides on poles 131a and 131b. Crank 214, turning screw 215 may be used for adjusting the height. Optional locking screws 216a and 216b may be used for securing bridge 130 to poles 131a and 131b, respectively.

In the depicted exemplary embodiment, rigid X-ray shield 118 may be set in upward position (as seen in FIG. 1) or in lower (operational) position (as seen in FIG. 2) by means of at least one pivot 120 (for drawing clarity, only one of the two pivots is marked in this figure). Optionally, a securing pin (not seen in this figure) is inserted to holes 121 and 122, thus securing the rigid X-ray shield 118 in the upward position.

It is noted that a man skilled in the art of mechanical engineering may find equivalent ways to provide at least some of the degrees of freedom of X-ray shield 118 in respect to the patient such as: linear motion along the bed, height above the bed, and orientation.

Figure 3:
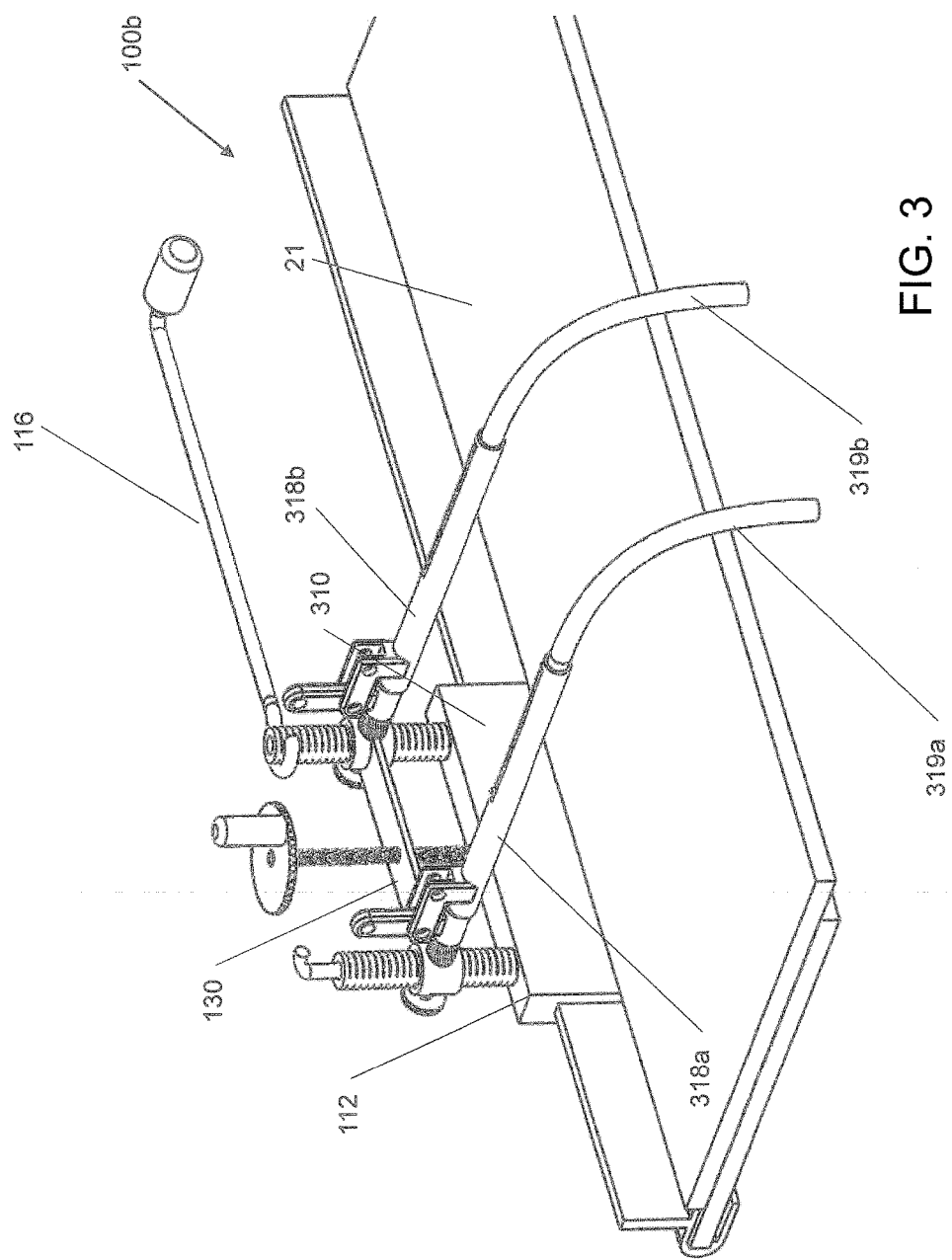
FIG. 3 schematically depicts medical system with a movable shield apparatus 100b for reducing radiation exposure of medical personnel according to another exemplary embodiment of the current invention.

FIG. 3 schematically depicts medical system with a movable shield apparatus 100b for reducing radiation exposure of medical personnel according to another exemplary embodiment of the current invention.

Movable shield apparatus 100b is similar in its construction and operation to the apparatus 100a of FIGS. 1 and 2, and thus only some of the differences will be disclosed herein.

In this exemplary embodiment, rail 110 which spans substantially the entire length of stretcher 21 is replaced with a shorted rail 310. Shorter rail 310 may optionally be connected to stretcher 21 in one location, or be moved along the stretcher depending on the patient size, positioning and the type of medical procedure. Shorter rail 310 may be lighter and thus easier to mount and removed.

In this exemplary embodiment, rigid X-ray shield 118 is replaced with two arms 318a and 318b which are connected to bridge 130 and are used for supporting an X-ray opaque blanket (not seen in this figure) that blocks the scattered X-ray photons from the patient.

In the depicted exemplary embodiment, arms 318a and 318b are attached to bridge 130 without pivots 120. However, it should be noted that pivots may be used for providing upward position to arms 318a and 318b. Operationally, more than two arms may be used for supporting the X-ray opaque blanket. Optionally, arms 318x (x stands for a, b, etc) may be connected together such that their orientation is kept the same in the case a pivot is used.

Optionally, arms 318x may comprise a curved section 319x for keeping the blanket away from the patient. Optionally, curved section 319x are made of flexible or elastic material.

Figure 4:
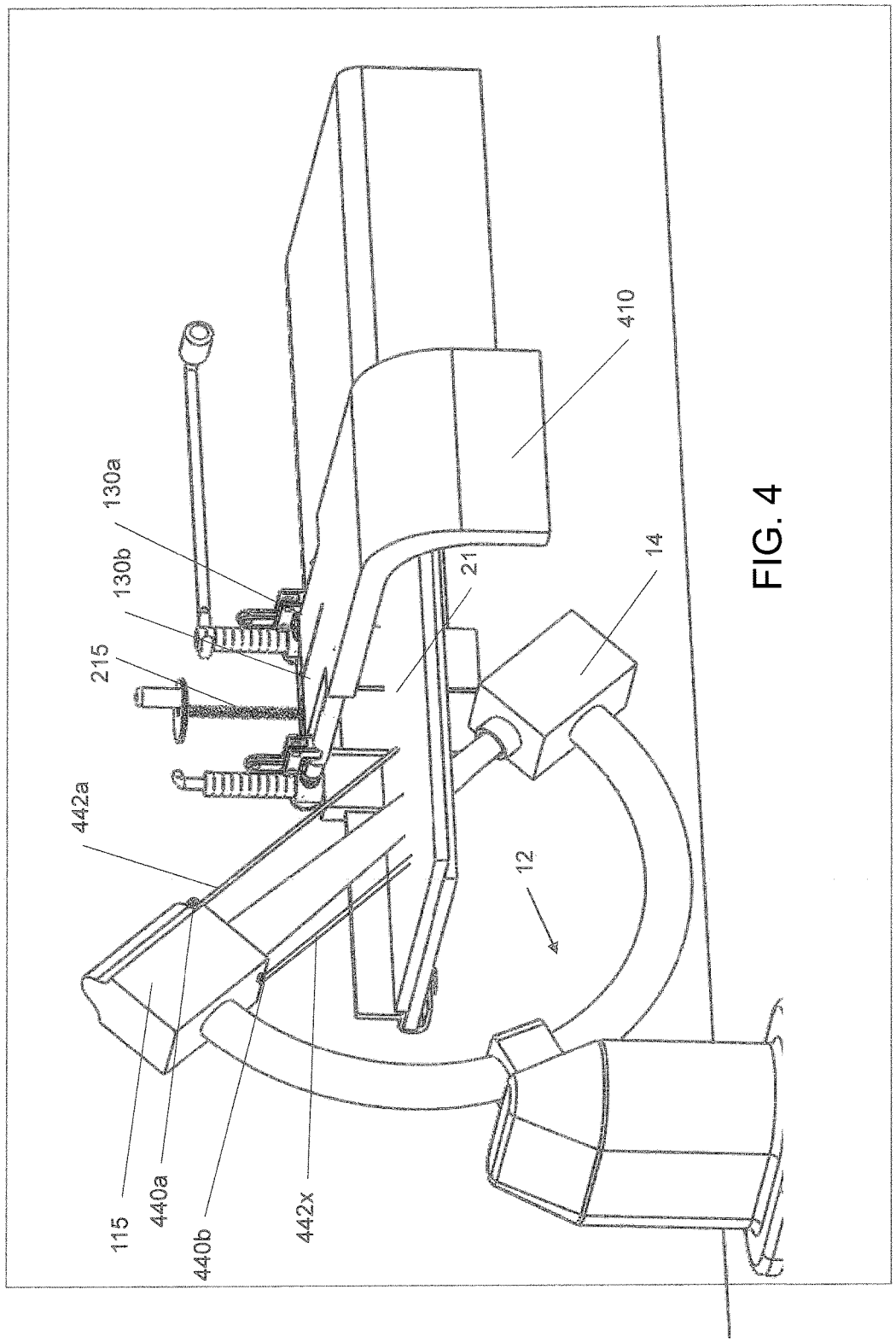
FIG. 4 schematically depicts another view of medical system with a movable shield apparatus for reducing radiation exposure of medical personnel seen in FIG. 3 according to yet another exemplary embodiment of the current invention.

FIG. 4 schematically depicts another view of medical system with a movable shield apparatus 100b for reducing radiation exposure of medical personnel seen in FIG. 3 according to yet another exemplary embodiment of the current invention.

In this figure, X-ray opaque blanket 410 is seen draped over arms 318x. Optional X-ray shielding blanket or strips 130x are seen as part of blanket 410, and the notch between them is used for passing screw 215.

In this figure X-ray tube 14 is positioned below the bed 21 and X-ray imager 115 is positioned above the bed. Optionally at least one visual indicator 440a, attached to the X-ray imager 115 is used to produce the at least one a light beam 442a. Beam 142a is situated to mark the edge of X-ray beam 18 and is used by the operator to ensure that X-ray beam 18 is not obscured by blanket 410 (or other shields used in this invention) without having to turn on the C-arm unit 11 and expose the patient and the medical personnel to harmful X-ray radiation. Optionally additional visual indicators 440x (such as the depicted indicator 440b) are used to produce the additional light beams 442x marking other edges of X-ray beam 18. For example, indicator 440x may be located at all four corners of X-ray imager 115.

Figure 5:
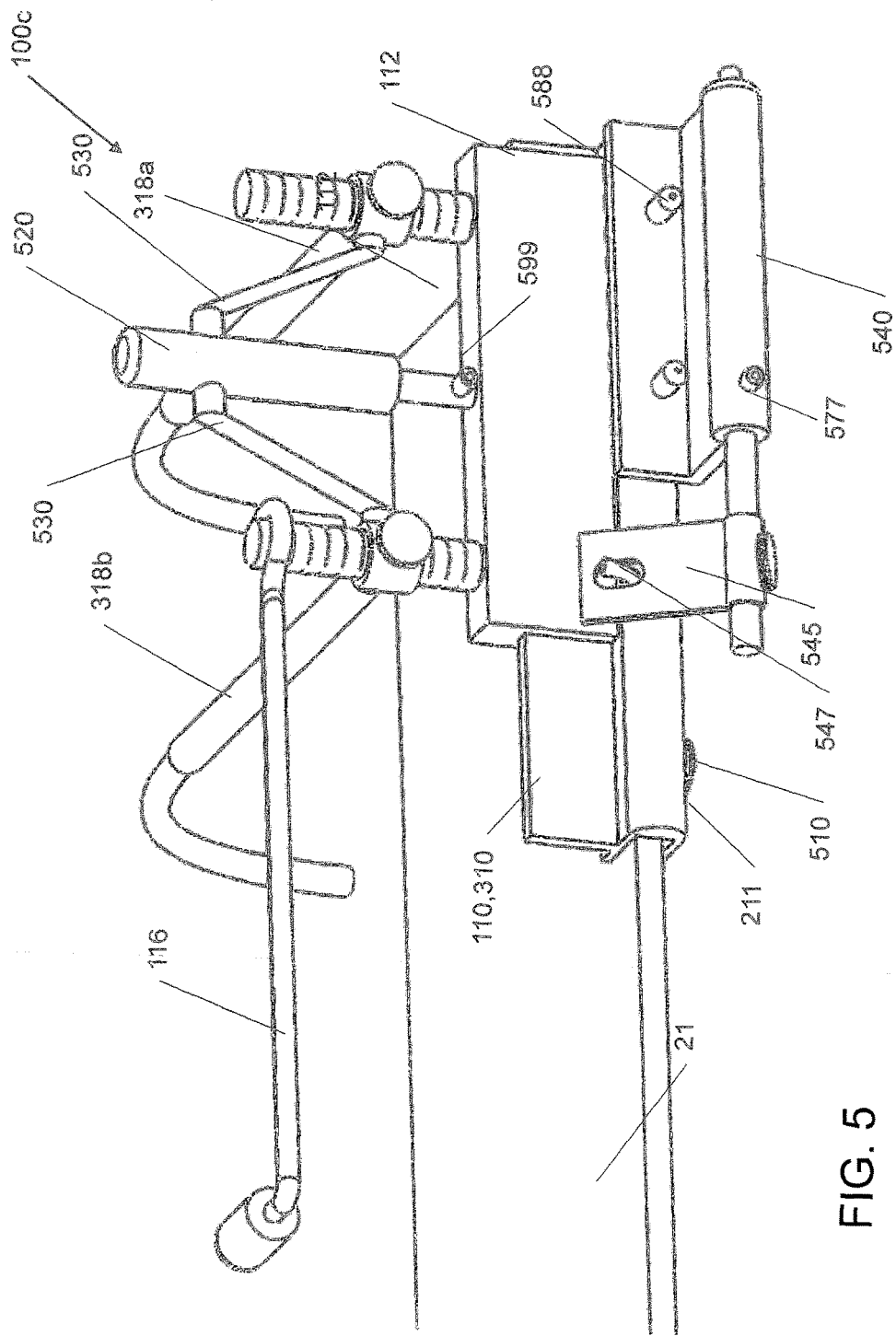
FIG. 5 schematically depicts medical system with a movable shield apparatus for reducing radiation exposure of medical personnel having motorized motion according to another exemplary embodiment of the current invention.

FIG. 5 schematically depicts medical system with a movable shield apparatus 100c for reducing radiation exposure of medical personnel having motorized motion according to another exemplary embodiment of the current invention.

Movable shield apparatus 100c is similar in its construction and operation to the apparatus 100a and 100b of FIGS. 1 to 4, and thus only some of the differences will be disclosed herein. It should be noted that any of embodiments 100a and 100b and combination thereof may be motorized.

Seen in this figure is the optional at least one fastener 510 that secures the rail (310, 110) to stretcher 21.

Elevation of arms 318x may be adjusted by motorized actuator 520 connected to the arm via bridge 530 on one side and to bridge 112 on the other side. Optionally, actuator 510 is a hydraulic piston or pneumatic piston. In the figure, hose connection 5599 is schematically seen. Alternatively actuator 520 is an electric motor with a nut and screw combination. For drawing clarity, other essential or optional parts of the actuation system such as controls components, power supply, pump, connecting cables or hoses, safety elements and the likes are not seen in this figure.

Position of carriage 112 along rail 310 (110) may be adjusted by motorized actuator 540 connected with connectors 588 to the rail on one side, and via joint 545 to carriage 112 on the other side. Optionally, actuator 540 may be a hydraulic cylinder and piston or pneumatic piston. In the figure, hose connection 577 is schematically seen. Alternatively, actuator 540 is an electric motor with a nut and screw combination. For drawing clarity, other essential or optional parts of the actuation system such as controls components, power supply, pump, connecting cables or hoses, safety elements and the likes are not seen in this figure.

Optionally, joint 545 is connected to cartridge 112 by a quick release connector such as protrusion in a notch assembly 547. By disconnecting actuator 540 from bridge 112 the entire bridge and X-ray shield may be moved along the rail for rapid access to the patient.

Optionally, handle 116 is missing.

Figure 6:
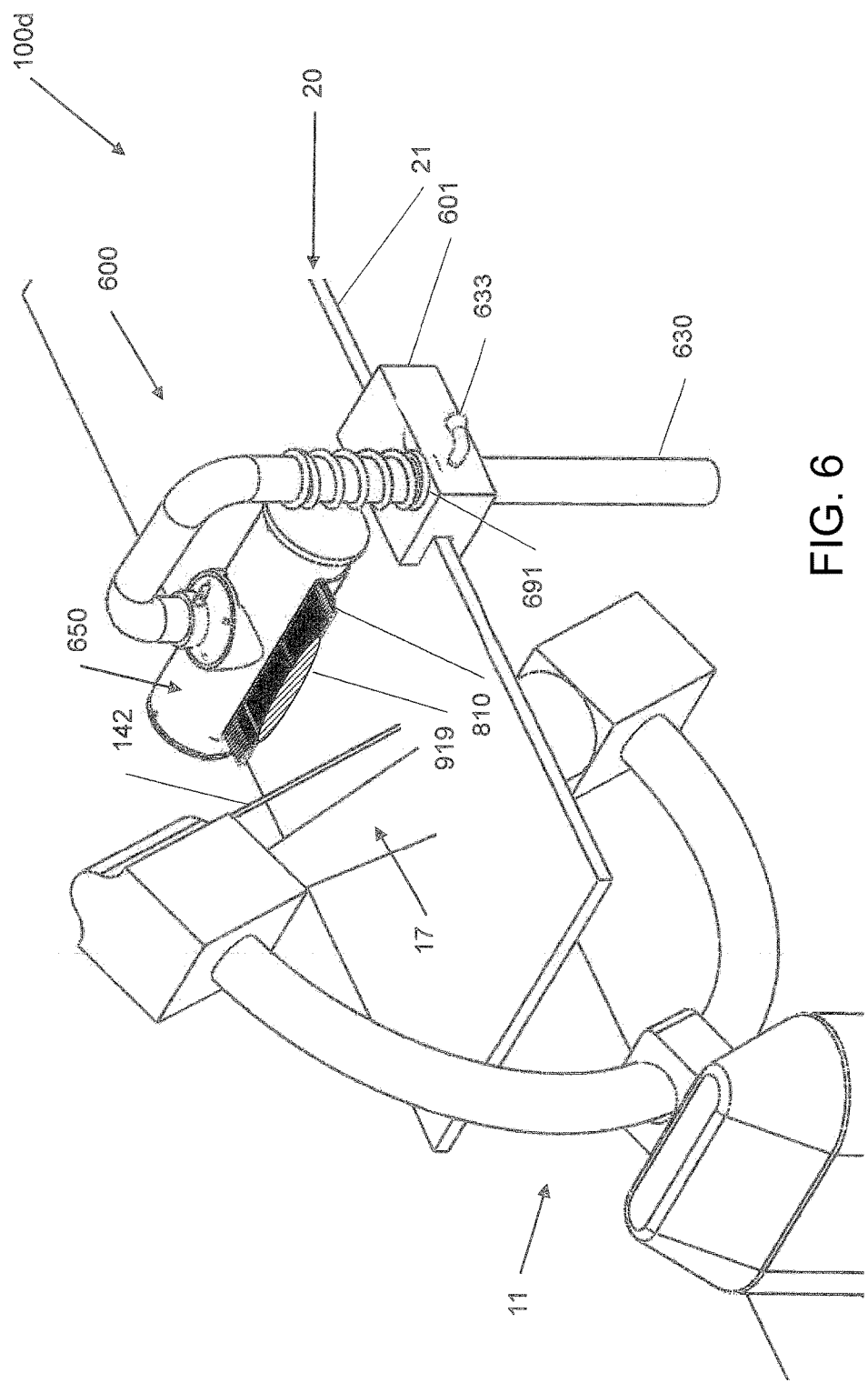
FIG. 6 schematically depicts medical system with shield apparatus for reducing radiation exposure of medical personnel having extendable, self-supporting X-ray opaque blanket, according to yet another exemplary embodiment of the current invention.

FIG. 6 schematically depicts medical system 100d with shield apparatus 600 for reducing radiation exposure of medical personnel having extendable, self-supporting X-ray opaque blanket, according to yet another exemplary embodiment of the current invention.

Figure 7:
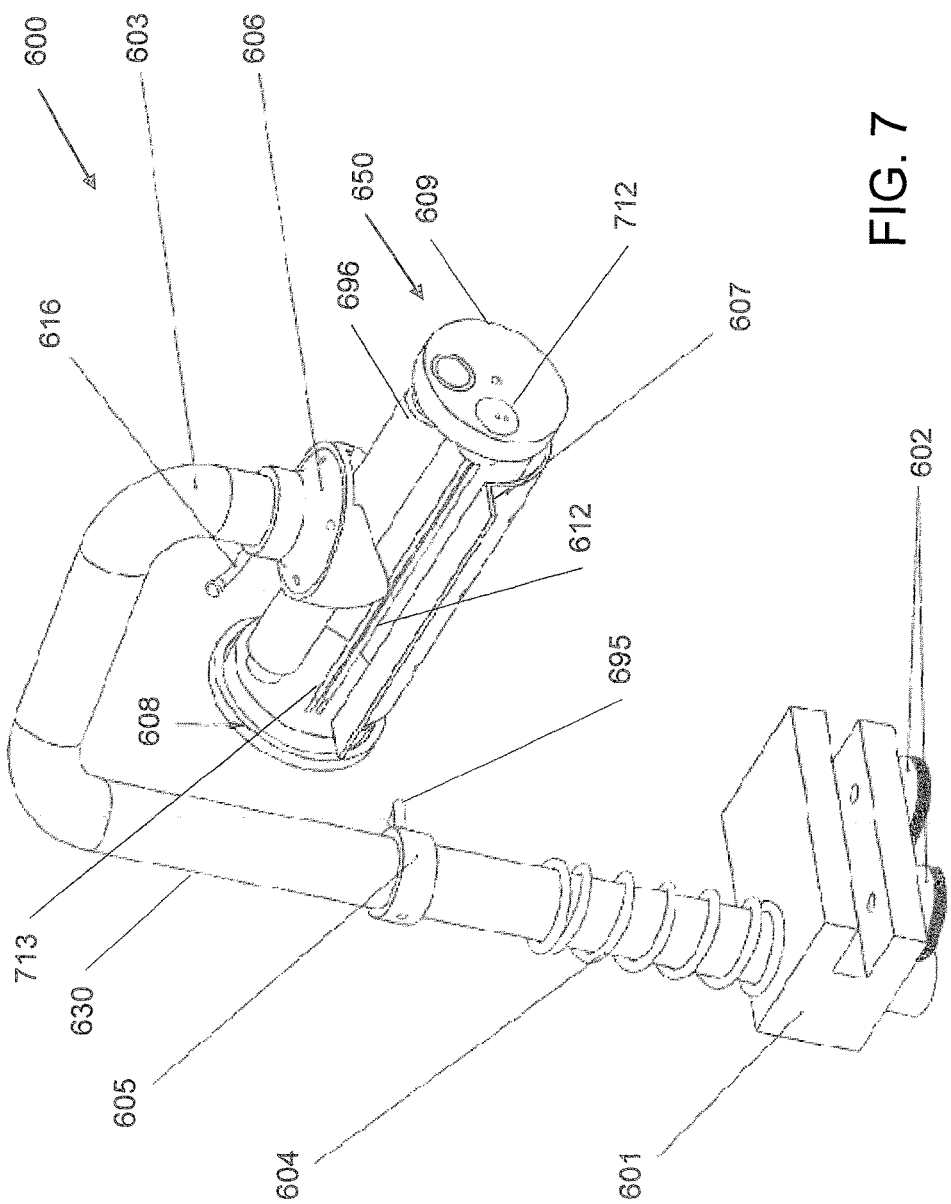
FIG. 7 schematically depicts some details of the apparatus for reducing radiation exposure of medical personnel having extendable, self-supporting X-ray opaque blanket, according to yet another exemplary embodiment of the current invention.
Figure 8:
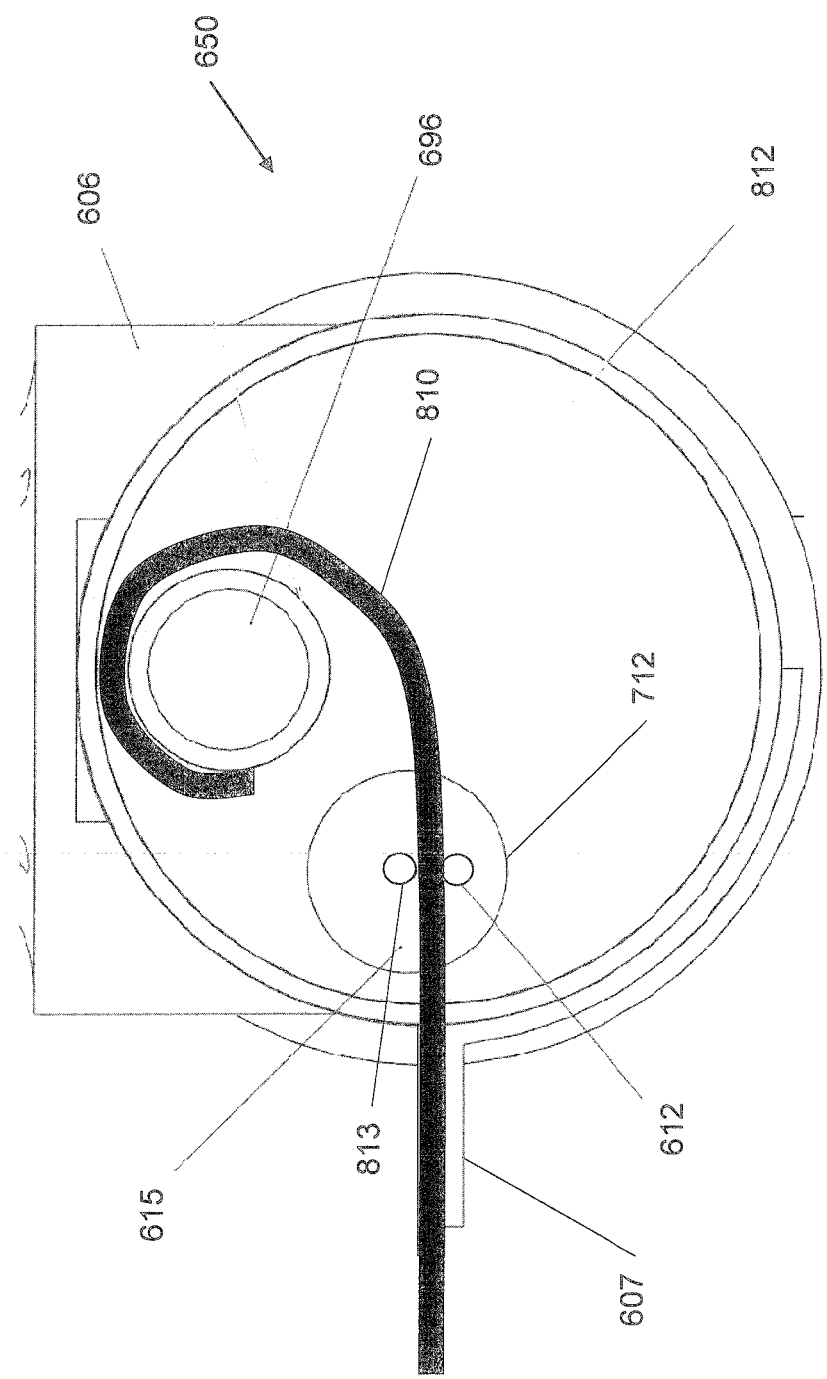
FIG. 8 schematically depicts a cross sectional view of the apparatus for reducing radiation exposure of medical personnel having extendable, self-supporting X-ray opaque blanket, according to yet another exemplary embodiment of the current invention.

FIG. 7 schematically depicts some details of apparatus 600 for reducing radiation exposure of medical personnel having extendable, self-supporting X-ray opaque blanket 810, according to yet another exemplary embodiment of the current invention. In this figure the outer cover 812 of dispenser body 650 of apparatus 600, and the X-ray opaque blanket 810 are not drawn to reveal some internal elements FIG. 8 schematically depicts a cross sectional view of apparatus 600 for reducing radiation exposure of medical personnel having extendable, self-supporting X-ray opaque blanket, according to yet another exemplary embodiment of the current invention.

Figure 9:
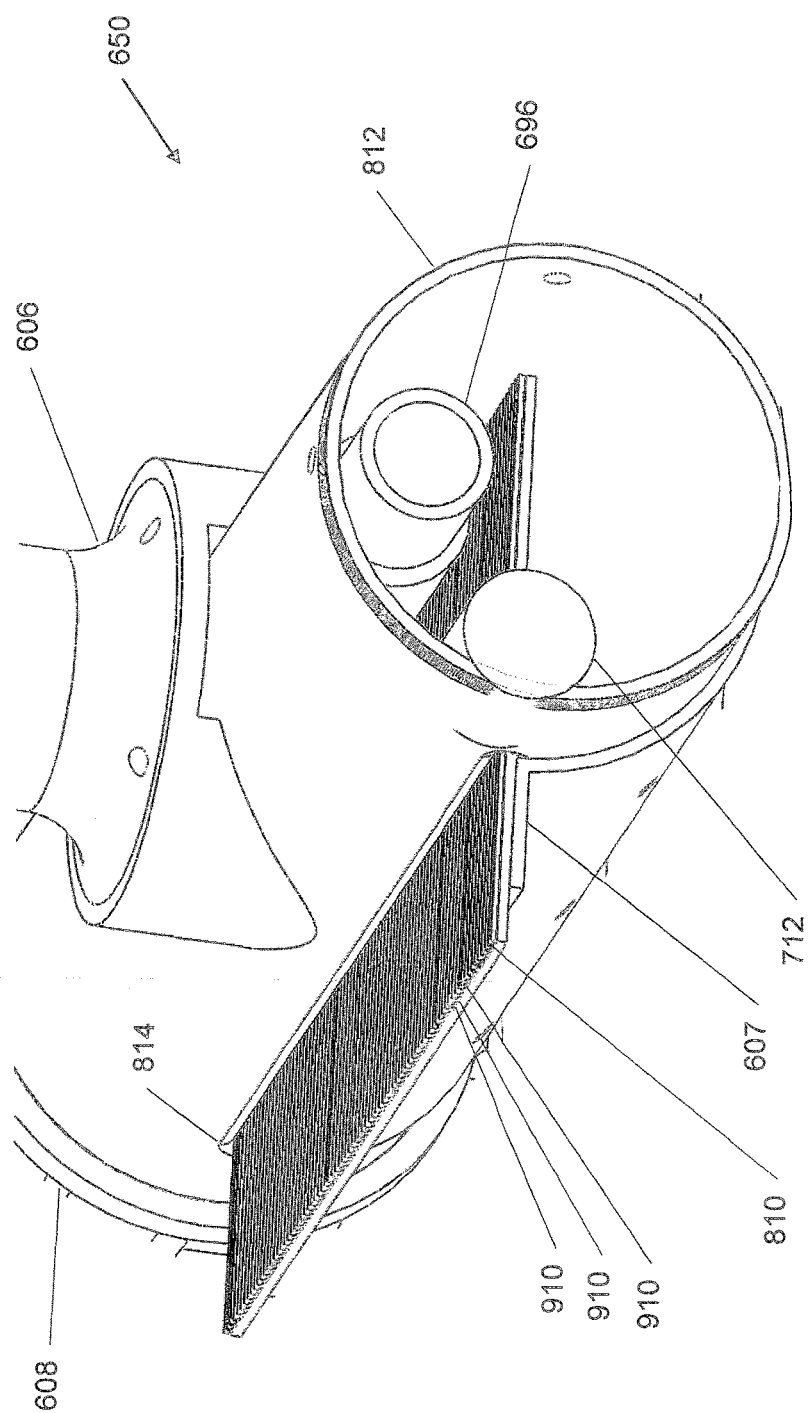
FIG. 9 schematically a view of the apparatus with one side cover removed, according to an exemplary embodiment of the current invention.

FIG. 9 schematically a view of apparatus 600 with one side cover removed, according to an exemplary embodiment of the current invention.

Figure 10:
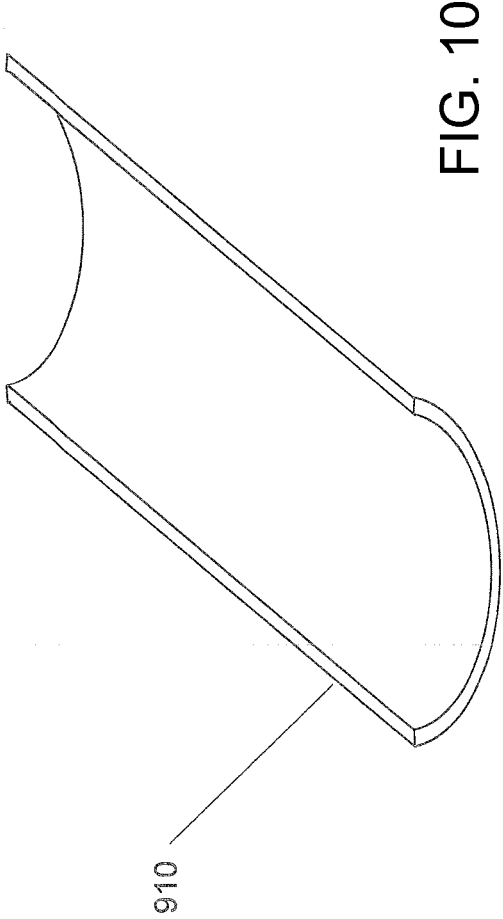
FIG. 10 schematically a view of a supporting spring used in self-supporting X-ray opaque blanket, according to an exemplary embodiment of the current invention

FIG. 10 schematically a view supporting spring 900, used in self-supporting X-ray opaque blanket 810, according to an exemplary embodiment of the current invention.

Referring now to FIGS. 6-10, system 100d comprises a C-arm unit 11 and a bed 20 having a table 21 as disclosed above. The inventive shield apparatus having extendable, self-supporting X-ray opaque blanket 600 for reducing radiation exposure of medical personnel, according to yet another exemplary embodiment of the current invention is attached to the patient table 21. Shield apparatus 600 is connected to table 21 by base 601 which attaches to table 21 using screws 602.

Pole 630 is inserted into a matching hole 691 in base 601 such that the pole may move up and down in respect to the base 601 within hole 691. Optionally, pole 630 may swivel within hole 691. Optional spring 604, at least partially support the weight of the device, making it easier to raise the device, and preventing or reducing the probability of the device falling on the patient when attempting to adjust its height. Locking ring 605, or other locking mechanism such as fastener 633 may be used to lock the pole 630 to base 601 at a desired height. For example, ring 605 may be locked to pole 630 by inserting pin 695 into one of a plurality of holes in pole 630 (holes in pole are not seen in the figure).

Optionally, pole 630 may rotate in hole 691 to swing the device away from the patient to allow immediate or emergency access to the patient, or easy dismount of the patient from the table.

Optionally, pole 630 has a bent 603 on which the dispenser 650 for X-ray opaque blanket is connected. Optionally, dispenser 650 is connected to pole 630 by a swivel joint 606 that allows rotating the dispenser 650 as needed. Optional swivel lock 616 may be used for locking the swivel joint 606 against inadvertent swivel.

Dispenser 650 comprises a cylindrical outer cover 812 and two side walls 608 and 609. X-ray opaque blanket 810 is wrapped around the retracting motor 696, and is attached to the retracting motor at its proximal end. By Clock Wise (CW) rerating of retracting motor 696, blanket 810 is pulled back into dispenser 650. The distal end of blanket 810 extends out of the body of dispenser 650 through an opening 814 in the cover 812. Blanket 810 rests on extending rotor 612 which may rotate in a Counter Clock Wise (CCW) direction to extend blanket 810 out of the dispenser 605. Preferably, extending rotor 612 is 4 mm in diameter. Motorized rotation of extending rotor 612 is done by activation of extending motor 712. Pressure rotor 813 keeps blanket 810 in contact with extending rotor 612.

X-ray opaque blanket 810 comprises a plurality of reed springs 910 that keeps the blanket in horizontal position when extended, yet allow the blanket to bend as it wrapped around retracting motor 696. X-ray opaque blanket 810 further comprises a flexible sheet of X-ray opaque material as known in the art, and a plastic cover (these elements are not marked in the drawing for drawing clarity). Reed springs 910 are in the shape of elongated metal strips having a trough shape such as seen in FIG. 10 and as used in retractable measuring tapes. It was verified that a commercially available retractable measuring tape may support up to 1.5 kilogram. The number of reed springs 910 may be determined according to the length of blanket 810 and its weight. Lip 607 help supporting blanket 810 in horizontal position when extended out of dispenser 650.

Controls of motors 712 and 696 may be done with manual switches, a remote control or foot pedals (not seen in these figures for drawing clarity). Optionally, manual levers (not seen in these figures) may be used for manually retracting (and optionally for extending) blanket 810 in case of power failure or motor dysfunction.

Optionally, a light sensor 919 is used for detecting light beam 142 and indicates that blanket 810 is near or within the X-ray beam 17. Specifically, sensor 919 may be useful for automatically positioning blanket 810 by commanding motors 696 and 712, or for automatically repositioning blanket 810 after adjusting the C-arm 11. Alternatively, sensor 919 in an X-ray sensor, adapted to detect X-ray emitted from the X-ray source and to distinguish between such intense X-ray beam from the weaker scattered radiation. By advancing the shield and the sensor to the edge of the X-ray beam (17 and 18), adequate protection from scattered radiation and minimal interference with the X-ray imaging may be achieved.

In yet another exemplary embodiment, control of the location of the shield along the bed is achieved by observing the X-ray image. The shield is actuated to move toward the C arm 11 until some blocking of the X-ray beam is observer, and away from C arm 11 if no blocking of the X-ray beam is observer. Optionally, the control is automatic and is performed by an image processing unit.

Proof of Concept and Experimental Verification:

Experiments were performed at sunnybrook health sciences centre—Toronto, Ontario, Canada by Dr. Osherov Azriel and Normand Robert. These experiments support the ability of lead rectangle to reduce the radiation emitted from the patient towards the operator.

Below is a summary of few of the important experiments and published manuscripts that support the idea that covering part of the patient surface area in the catheterization laboratory will reduce the exposure to scattered radiation to the medical personnel in the room.

i) Since 2009, Dr. Osherov developed a novel lead rectangle to help reduce the scattered radiation exposure in the catheterization laboratory. An unfortunate early death of a close colleague who died from left side brain tumor (glioblastoma multiforme), apparently due to almost 18 years of radiation exposure, led Dr. Osherov to invest time and effort developing ways to solve the problem. A recent paper (Roguin et al) reported new cases and reviewed the literature describing many interventional cardiologists who died from brain tumor. With the help of Dr. Normand Robert a lead rectangle was shown to be efficient in reducing the radiation exposure. The first studies were done using conventional fluoroscopy equipment and the RANDO® phantom. The radiation was detected by several dosimeters at different distances (50 and 100 cm) from the radiation beam. A lead skirt (two layers of 0.25 mm) was folded into the shape of a lead rectangle shield with final dimensions of 60×100 cm. This shield was used to cover the phantom's "umbilicus" and down. A summar-ization of the result is presented here. In a cranial (25 degrees) Anterior-Posterior projection, there was a 93.5% reduction at 50 cm from the beam (121.4±16.9 vs. 7.9±2.5 mRem), and 69.5% reduction at 100 cm distance (32.7±1.4 vs. 10.0±2.0 mRem) respectively. In a left anterior-oblique projection (39 degrees with 26 degrees cranial), more than 90% reduction was demonstrated at 50 and 100 cm from the radiation beam respectively (123.5±26.4 to 1.4±17.9 and 74.9±17.9 to 2.4±5.9 mRem respectively). In a cumulative dose of DAP of 60,000 $cGy/Cm^2$ in three views a similar significant reduction in scattered radiation was noted: 95% and 82.3% at 50 and 100 cm respectively (302.8±26.8 to 15±21.8 and 156±19.9 to 21.4±11.4 mRem).

Few advantages of the invention (movable X-ray shield apparatus) over a simple lead rectangle are presented here.

1) In caudal views, there are times when the simple rectangle obstruct the radiation field, and need to be moved. According to embodiments of the current invention, moving the device according to the light/laser beam and or radiation detector will prevent obstructing the radiation beam and the fluoroscopy image in any view taken.

2) The simple lead rectangle will cover the patient from the umbilicus and down thus leaving large part of the patient uncovered (e.g., the chest) which is a source for scattered radiation. This will be blocked or absorbed using the patent.

Both the lead rectangle and the patent describe can be made sterile with the use of a simple sterile nylon bag thus making the device compatible with the most restricted infection control regulation used today in the catheterization laboratory.

ii) Lange et al., using a pelvic lead shielding, studied the reduction of operator radiation exposure during cardiac catheterization via the radial access in comparison with the femoral access. They demonstrated For radial access, operator dose decreased from 20.9±13.8 µSv to 9.0±5.4 µSv, p<0.0001 with pelvic lead shielding. For femoral access, it decreased from 15.3±10.4 µSv to 2.9±2.7 µSv, p<0.0001. Their results showed that pelvic lead shielding is highly effective in reducing operator radiation exposure for radial as well as femoral procedures. However, despite its use, radial access remains associated with a higher operator radiation dose.

The caveats with the "pelvic lead shielding" are: 1) It might obstruct the image during fluoroscopy causing increase in radiation given to the patient and medical personnel. 2) There is less protection for radial access procedures probably due to holes in the lead shielding in the femoral access area. 3) Due to the femoral access holes and the need for a complex sterile bag design—there are infection control issues that were not answered in the paper published iii) Radpad® scatter protection is a sterile, disposable bismuth-barium radiation shield drape measure 30×40 cm that should be able to decrease the dose of operator radiation during diagnostic and interventional procedures. Politi et al. using the Radpad® demonstrated that the mean total radiation exposure to the operator was lower when Radpad was utilized (282.8±32.55 μSv vs. 367.8±105.4 μSv, P<0.0001) corresponding to a 23% total reduction. The main Caveat of this Radpad® drape 1) its small area (30×40 cm) covering only small portion of the patient area leading to a smaller reduction in radiation detected/exposure. 2) The Radpad® needs to be moved manually if it is obstructing the image during fluoroscopy. 3) The device is disposable and cannot be reused.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

The invention claimed is:

1. A movable shield apparatus for a fluoroscopy system comprised of an X-ray fluoroscopy bed having a patient table and a C-arm unit, wherein the C-arm unit comprises a source for an X-ray beam, an X-ray imager, and at least one light source, the movable shield apparatus comprising:

an X-ray opaque shield for reducing radiation exposure to medical personnel;
at least one sensor configured to determine an edge of the X-ray beam by sensing the at least one light source;
a rail capable of being connected to the patient table;
a carriage capable of sliding along said rail;
at least one pole connected substantially vertically to said carriage; and
a bridge capable of sliding along said at least one pole,
wherein the X-ray opaque shield is supported by said bridge with at least one pivot to block scattered X-ray radiation, and
wherein the movable shield apparatus is configured to move along the patient table.

2. The movable shield apparatus of claim 1, wherein the X-ray opaque shield comprises an X-ray opaque blanket, and wherein the X-ray opaque blanket is supported by at least one arm connected to the bridge.

3. The movable shield apparatus of claim 1, further comprising a motorized actuator capable of moving the carriage along the rail.

4. The movable shield apparatus of claim 1, further comprising a motorized actuator capable of moving the bridge along the at least one pole.

5. The movable shield apparatus of claim 1, further comprising a handle for moving the X-ray movable shield apparatus along the rail, wherein said handle is capable of unlocking the shield apparatus from the rail.

6. A movable shield apparatus for a fluoroscopy system comprised of an X-ray fluoroscopy bed having a patient table and a C-arm unit, wherein the C-arm unit comprises a source for an X-ray beam, an X-ray imager, and at least one light source, the movable shield apparatus comprising:

an X-ray opaque shield for reducing radiation exposure to medical personnel;
at least one sensor configured to determine an edge of the X-ray beam by sensing the at least one light source;
a base capable of being connected to the patient table;
a pole connected substantially vertically to said base; and
a dispenser for dispensing the X-ray opaque shield, wherein the dispenser is supported by said pole,
wherein said X-ray opaque shield is a self-supporting X-ray opaque blanket capable of being extended from said dispenser, and
wherein the movable shield apparatus is configured to move along the patient table.

* * * * *